United States Patent
Casset et al.

(10) Patent No.: US 6,912,421 B2
(45) Date of Patent: Jun. 28, 2005

(54) DETECTION OF A RISK OF A FUSION SITUATION IN AN ACTIVE IMPLANTABLE MEDICAL DEVICE

(75) Inventors: Cyril Casset, Paris (FR); Marcel Limousin, Paris (FR)

(73) Assignee: ELA Medical S.A., Montrouge (FR)

( * ) Notice: Subject to any disclaimer, the term of this patent is extended or adjusted under 35 U.S.C. 154(b) by 234 days.

(21) Appl. No.: 10/008,609

(22) Filed: Nov. 8, 2001

(65) Prior Publication Data

US 2002/0095183 A1 Jul. 18, 2002

(51) Int. Cl.⁷ .............................................. A61N 1/368
(52) U.S. Cl. .................................................... 607/28
(58) Field of Search ................................ 607/27, 28, 9

(56) References Cited

U.S. PATENT DOCUMENTS

| | | | |
|---|---|---|---|
| 5,527,347 A | * | 6/1996 | Shelton et al. ............. 607/9 |
| 5,534,016 A | | 7/1996 | Boute ............................ 607/9 |
| 5,626,620 A | | 5/1997 | Kieval et al. ................. 607/9 |
| 5,713,930 A | | 2/1998 | Van der Veen et al. ..... 607/25 |
| 5,861,007 A | | 1/1999 | Hess et al. ..................... 607/9 |
| 6,456,881 B1 | * | 9/2002 | Bornzin et al. ............... 607/27 |

FOREIGN PATENT DOCUMENTS

| | | | |
|---|---|---|---|
| EP | 0 597 728 A3 | 5/1994 | ......... A61N/1/368 |
| EP | 0 597 728 A2 | 5/1994 | ......... A61N/1/368 |
| WO | 93/02741 | 2/1993 | ........... A61N/1/36 |

* cited by examiner

Primary Examiner—Kennedy Schaetzle
(74) Attorney, Agent, or Firm—Orrick, Herrington & Sutcliffe LLP

(57) ABSTRACT

An active implantable medical device, in particular a pacemaker, defibrillator, cardiovertor, or a multisite device including detection of a risks of a fusion situation. This device is of the double chamber type, and it detects atrial and ventricular events, provides atrial and ventricular stimulation, and delivers a ventricular stimulation pulse after expiration a programmed atrio-ventricular delay (AVD) following the detection of an atrial event (P, A), and in the absence of detection of a ventricular spontaneous event (R) within the AVD. A fusion situation is detected based on an analysis of a sequence of successive cardiac cycles for which the atrio-ventricular delay is modified from one cycle to the next (AVD, AVD+31, AVD+63). The presence or the absence of a ventricular spontaneous event (R) occurring inside the atrio-ventricular delay thus modified is determined, and the existence of a risk of fusion is determined in the event of the occurrence of a spontaneous ventricular event during at least one of the cardiac cycles of the sequence. The detected risk of fusion can be used to control the operation of implant.

6 Claims, 3 Drawing Sheets

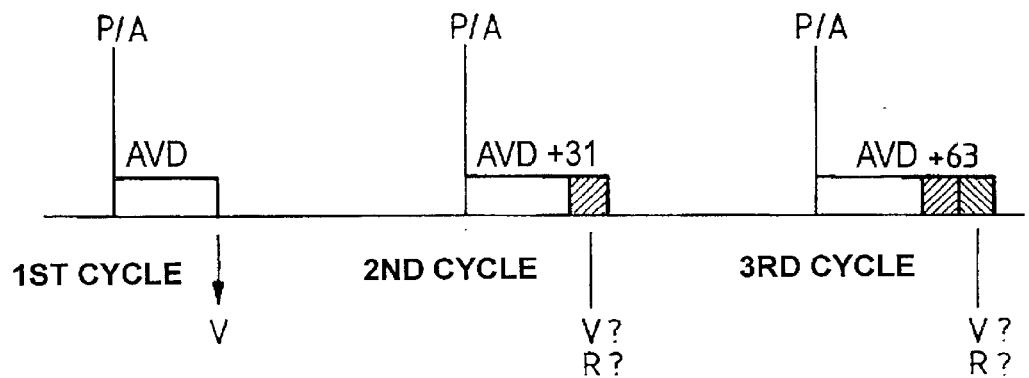
FIG_1
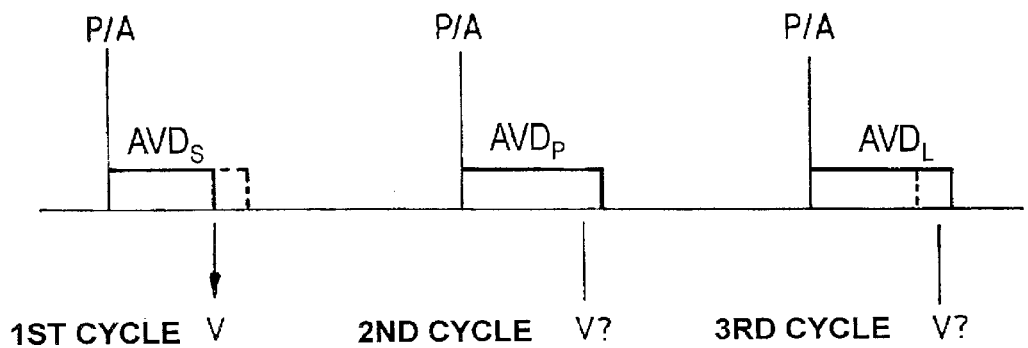
FIG_3

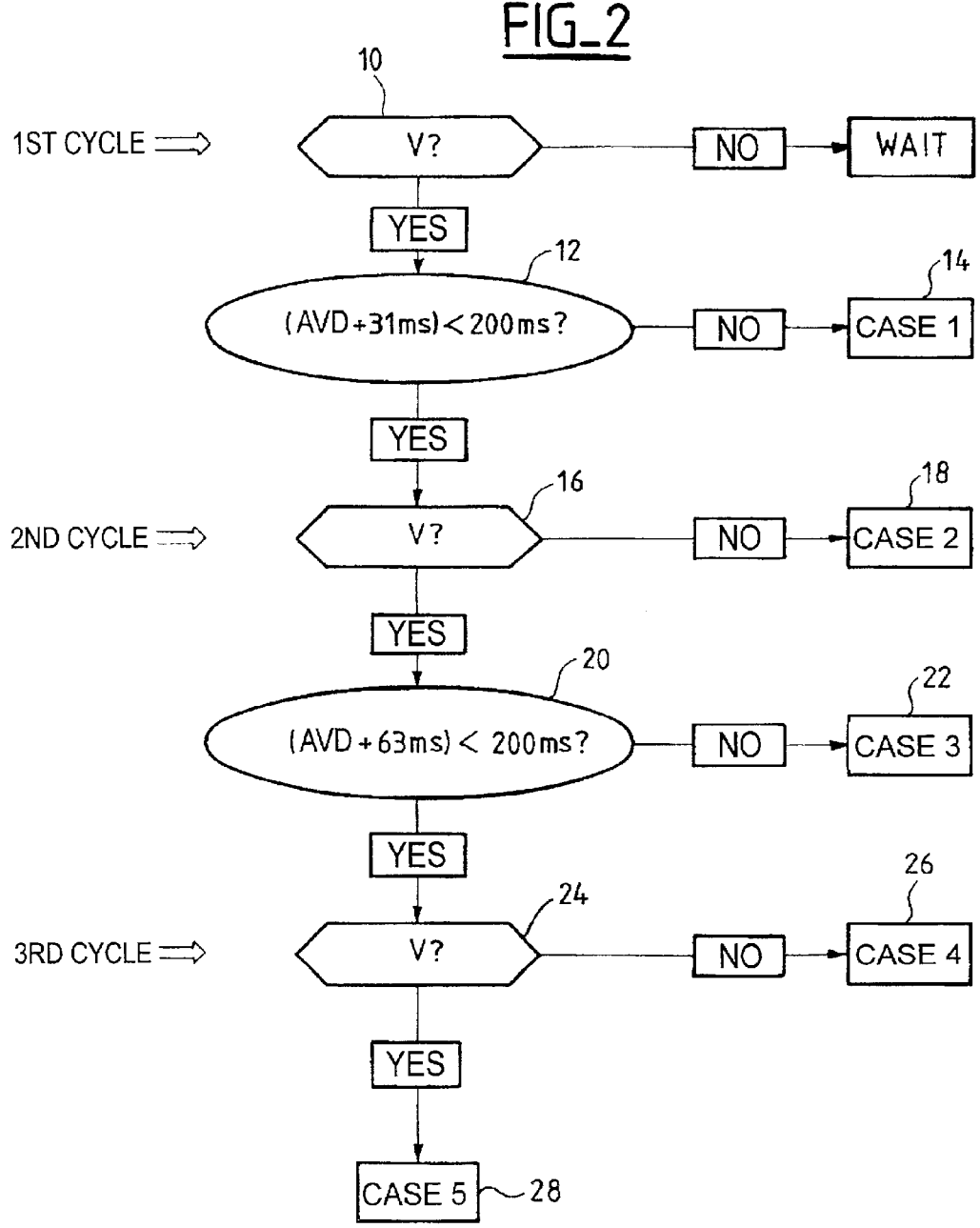

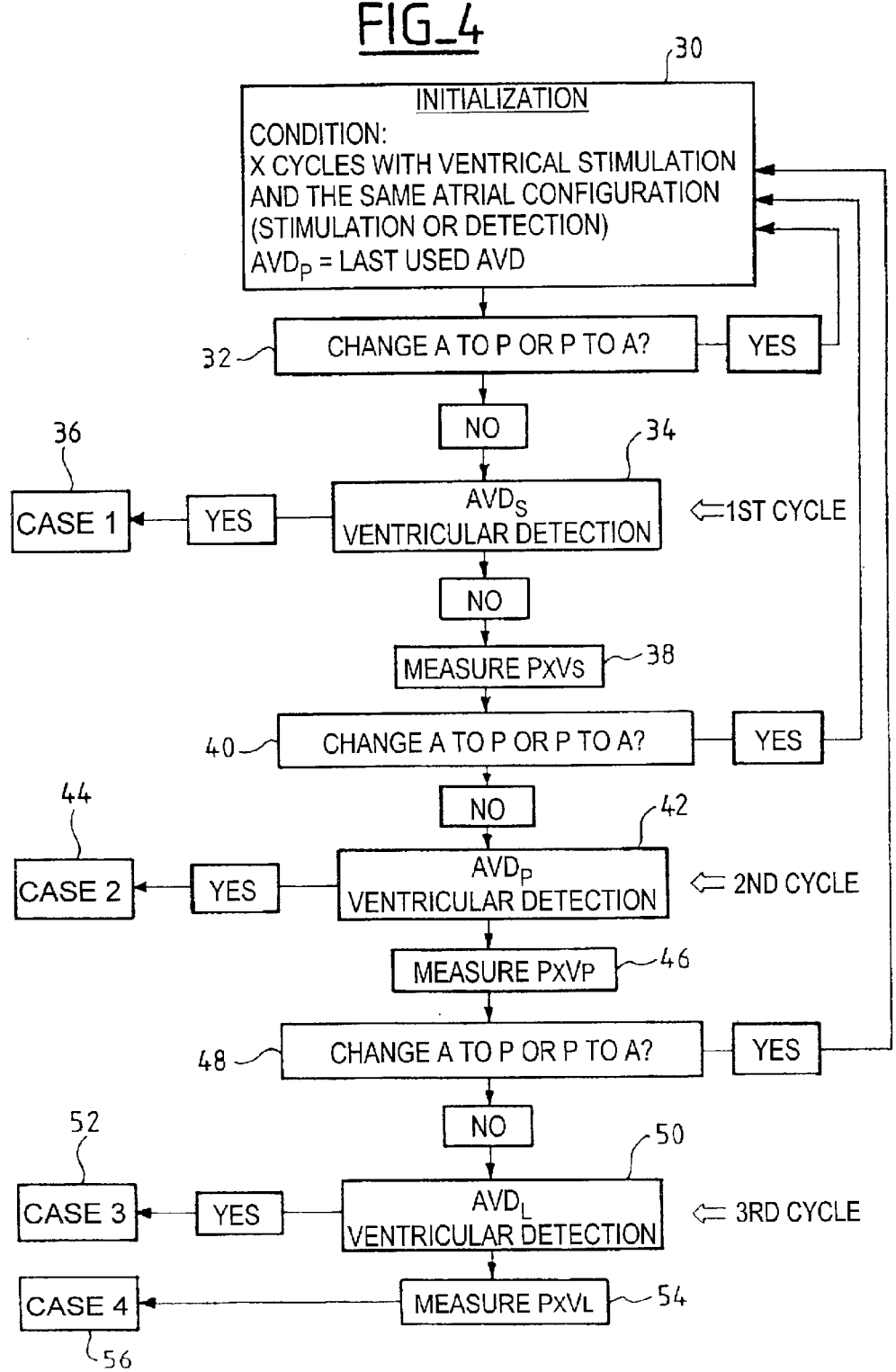

DETECTION OF A RISK OF A FUSION SITUATION IN AN ACTIVE IMPLANTABLE MEDICAL DEVICE

FIELD OF THE INVENTION

The present invention is directed to "active implantable medical devices" as such devices are defined by the Jun. 20, 1990 directive 90/385/CEE of the Council of the European Communities, and more particularly to pacemaker, "multisite devices", defibrillator and/or cardiovertor devices. The operation of these devices depends upon the detection of the cardiac signals spontaneously produced by the heart of the patient carrying the device, to record data, to pose a diagnosis or to apply an adapted therapy, typically while the device delivers to the heart low energy pulses for the treatment of disorders of the cardiac rhythm. The present invention also relates to prostheses of the "double chamber" type (i.e., a device in which it is possible to stimulate the right atrium and the right ventricle as in the known DDD configuration), the "triple chamber" type (right atrial stimulation and double ventricular stimulation), the "quadruple chamber" type (double atrial stimulation and double ventricular stimulation) and, in a general way, to prostheses known as "multisite," devices that comprise at least one atrial site and one ventricular site located on the same side of the heart.

BACKGROUND OF THE INVENTION

The control of cardiac stimulation implies a regular adjustment of various control parameters. The principal control parameters are the frequency of stimulation and the atrioventricular delay (AVD). These parameters, as well as the decision whether or not to stimulate a ventricle, rely on the control over the presence or absence of a spontaneous ventricular rhythm, associated with an atrial rhythm (that can itself be a spontaneous or stimulated rhythm).

Another control parameter regularly readjusted is the voltage level of the stimulation pulse delivered to the cardiac cavities, namely the ventricular or atrial cavities. This is because the voltage stimulation threshold, also called the "capture threshold", is a value that can vary with time and the device must deliver a stimulation pulse that exceeds the capture threshold to produce with certainty a depolarization of the myocardiac cavity. It is therefore desirable to be able to reevaluate at regular intervals the stimulation amplitude level by performing a test of the effectiveness of the stimulation threshold, called the "capture test."

An algorithm for automatically testing the ventricular capture threshold is described, for example, in patent publication WO-A-93/02741 and its corresponding U.S. Pat. No. 5,411,533 (assigned to Ela Médical, the assignee hereof). This algorithm also is used in commercial pacemaker products sold under the Talent™ brand available from Ela Médical, Montrouge, France. This test algorithm uses in particular the detection of the presence or absence of a spontaneous ventricular rhythm associated with a concomitant, spontaneous or stimulated, atrial rhythm.

A clinical follow-up of patients having devices using this algorithm has revealed that, in certain cases, the algorithm for controlling the pacemaker or the capture test algorithm is some times fooled by the occurrence of "fusions", i.e., stimulation pulses intervening in a concomitant way to a spontaneous ventricular depolarization. Indeed, after a ventricular stimulation, the detected ventricular event (a "QRS complex") can be either the direct result of this stimulation, taking into account the latency delay existing between these two events, or a spontaneous complex occurring in the same temporal window (i.e., a fusion). The occurrence of a fusion can have a deleterious effect from the point of view of the patient's hemodynamic condition, because of the presence of two contractions very close together of which one is essentially useless.

In the case of a capture test, even if a fusion does not have an adverse hemodynamic effect, it is nevertheless likely to produce an increase of the value of the capture threshold applied relative to the capture threshold actually needed by patient. This will result in a readjustment of the stimulation amplitude to a higher level than is necessary that will be maintained at least for several hours. Although the excessive level is not in itself dangerous, it does increase power consumption over what would be used with a lower stimulation amplitude, and thus reduces the useful lifespan of the implant.

OBJECTS AND SUMMARY OF THE INVENTION

It is an object of the present invention to provide an improved device by proposing a device equipped with a means for detecting a risk of fusion to allow the control algorithm to take an adapted action, for example, to inhibit the reprogramming of one or more pacemaker control parameters for operation of the pacemaker, and to repeat, for example, the capture test at a later time, such as after disappearance of the detected risk of fusion.

To this end, the invention broadly concerns an active implantable medical device of the known "double chamber" type, i.e., including means for detecting atrial events, means for detecting ventricular events, means for delivering atrial stimulation, and means for delivering ventricular stimulation, that is able to deliver a ventricular stimulation pulse after the passage of an atrio-ventricular programmed delay ("AVD") consecutive to an atrial event and in the absence of detection of a spontaneous ventricular event within this delay.

According to one aspect of the invention, such a device is provided with means for detecting a risk of fusion based on an analysis of a sequence of successive cardiac cycles in which the atrio-ventricular delay is modified from one cycle to the next, to detect the presence or the absence of a spontaneous ventricular event occurring inside the modified atrio-ventricular delay, and to determine the existence of a risk of fusion in the appearance of a spontaneous ventricular event during at least one of the cardiac cycles in the sequence.

In a first preferred embodiment, the atrio-ventricular delay is modified by successive lengthening of its duration, and the sequence includes at least three cardiac cycles.

In a second preferred embodiment, the atrio-ventricular delay is modified by shortening and lengthening the duration of the programmed atrio-ventricular delay, and the sequence includes at least three cardiac cycles with short and long programmed atrio-ventricular delays. In this second embodiment, when the device also comprises means for evaluating a capture threshold parameter, the means for detecting a risk of fusion (also referred to as a "fusion situation") preferably compares the values of the capture threshold parameter during successive cardiac cycles of the sequence, two by two, with the existence of a risk of fusion being established when at least two of these values are the same or within a percentage tolerance limit.

In the present invention, the means for detecting a fusion situation can advantageously include means for controlling, with each cardiac cycle, the stability of the atrial configuration, i.e., stimulated or spontaneous, and means for inhibiting the analysis of the sequence of successive cardiac cycles in the event that the configuration changes from a stimulated to a spontaneous configuration or vice versa.

The means for detecting a fusion situation can advantageously be used to inhibit, in the event of an established existence of a risk of fusion, the automatic measurement of the capture configuration by the means for evaluating a capture threshold parameter of the device.

BRIEF DESCRIPTION OF THE DRAWINGS

Further features, characteristics, and advantages of the present invention will appear to a person of ordinary skill in the art in view of the following description of a preferred embodiment of the invention, made with reference to the drawings annexed, in which:

FIG. 1 is a chronogram showing three successive cardiac cycles modified so as to allow the detection of a possible fusion, according to a first embodiment of the present invention;

FIG. 2 is a flow chart showing a process in accordance with the present invention;

FIG. 3 is a chronogram showing three successive cardiac cycles modified in accordance with a second embodiment of the present invention; and FIG. 4 is a flow chart showing a process in accordance with the present invention for implementing the embodiment of FIG. 3.

DETAILED DESCRIPTION OF THE INVENTION

With reference to FIG. 1, three successive cardiac cycles are represented, where the actions will be synchronized on an atrial event, which may be spontaneous (i.e., an atrial detection P) or stimulated (i.e., an atrial stimulation A). Initially, the atrio-ventricular delay (AVD) is fixed at its programmed value by the physician.

In the examples discussed herein, it is desirable to choose an AVD duration that is usable for the automatic determination of the capture threshold as described in WO-A-93/02741 and U.S. Pat. No. 5,411,533, but this application is not restrictive, and the method for detecting a risk of ventricular fusion according to the invention can be used for other purposes and in another context, for example, capture threshold tests other than what is described in the aforementioned patent.

With reference to FIG. 2, the process of the illustrated algorithm begins at stage 10 with determining if one clearly is in the presence of a situation where the ventricle must be stimulated (ventricular stimulation V) at the end of the programmed AVD. If so, the algorithm lengthens the AVD during the following cycles gradually, step by step, with each cycle. Lengthening is achieved, for example, by a fixed amount, in this example, 31 ms, within a maximum limit allowed for the ADV variation, for example, a 200 ms limit (stage 12). Alternatively, the maximum limit of the AVD can advantageously be determined as a function of the heart rate for which the test is carried out.

In the first case CASE 1, i.e., where the lengthening of the AVD would exceed the allowed maximum limit (stage 14), the AVD selected is too long and does not allow the device to control the presence of a spontaneous rhythm. For safety reasons then, the AVD is reduced, by an amount, such as to a value AVD−63 ms.

If, on the other hand, the lengthening of the AVD does not exceed the fixed maximum limit, then the algorithm detects during a second cardiac cycle the occurrence of a stimulated ventricular event (ventricular stimulation V) or spontaneous ventricular event (ventricular detection R) before the end of the AVD as lengthened by 31 ms (stage 16). The detection of a spontaneous ventricular event (CASE 2, stage 18) reveals a risk of fusion for the programmed AVD. As a result, the AVD is then fixed at a short value, preferably a minimal value, subject to satisfying the constraint that it be shorter than the programmed AVD by at least 60 ms.

In the event that there is a stimulated ventricular event during the second cardiac cycle, the AVD is lengthened once again, for example, to 63 ms greater than its programmed value, again staying within the limit of the allowed maximum value (stage 20). If it is not possible to increase the AVD without exceeding the maximum limit (CASE 3, stage 22), to take account of the risk of the occurrence of a spontaneous ventricular event at the end of the AVD (between AVD+31 ms and AVD+63 ms), then the AVD is fixed at a reduced value compared to the programmed value, typically reduced to AVD−31 ms.

If the AVD could be lengthened by 63 ms to examine a third cardiac cycle, the algorithm then tests the possible occurrence of a stimulated ventricular event before the end of the AVD lengthened by 63 ms (stage 24). The absence of such a stimulated event (case 4, stage 26) reveals a risk of fusion. Also, as in the preceding case, the AVD is then reduced compared to its programmed value, typically to AVD−31 ms. In the contrary case, i.e., in the absence of a ventricular detection in the 63 ms following the programmed AVD (CASE 5, stage 28), there is not a risk of fusion, and one can thus choose for the AVD a value AVD−31 ms compared to the programmed value.

With reference to FIGS. 3 and 4, an alternate embodiment of the present invention is illustrated, where the detection algorithm for the fusion situation is used in combination with an algorithm for measuring a capture parameter (parameter for the determination of the capture threshold) as described, for example, in the above mentioned WO-A-93/02741 and U.S. Pat. No. 5,411,533. The two parameters used in this embodiment are the capture parameter and the AVD. The AVD will take three different values during three successive cardiac cycles as illustrated in FIG. 3:

1) for the first cardiac cycle: AVD short (labeled "AVDs"): the value of the AVD is reduced, for example, by 31 ms, as compared to the value of the programmed AVD; alternatively, the AVD short can also be reduced to a given fixed value, for example AVDs=63 ms.

2) for the cardiac second cycle: Programmed AVD (labeled "AVDp"), i.e., the value of the AVD used by the pacemaker at the time of launching of the function for the detection of fusion.

3) for the third cardiac cycle: Long AVD (labeled "AVDl"): the value of the AVD is increased, for example, by 31 ms, as compared to the value of the programmed AVD.

The capture parameter is labeled "PxVy," x being the amplitude of the stimulation pulse (which may vary) and y being 1, s or p, according to whether measurement is taken with a long, short or programmed AVD, respectively.

The process implementing the algorithm, illustrated in FIG. 4, is as follows. With the precondition (stage 30), the process is initialized by securing that a certain number of cardiac cycles followed one another with the same configuration of stimulation/detection in the cavities of interest, for example, atrial stimulation and ventricular stimulation, or atrial detection and ventricular stimulation. In addition, the programmed AVD is initialized with the value of the last AVD used by the pacemaker under normal operation.

The following stage (stage 32) determines, first of all, whether or not the configuration changed, i.e., atrial stimulation (A) did not become an atrial detection (P), or the reverse. In the event of change of configuration, the test is stopped and the algorithm returns to the initialization stage 30, because the conduction is not the same in both cases (spontaneous or stimulated atrial event), and it is not possible to carry out a conclusive test.

If the configuration did not change, a first cardiac cycle is analyzed (stage 34, and first cardiac cycle of FIG. 3) with a shortened AVD, AVDs. The algorithm then waits for the occurrence of a spontaneous ventricular event. If no spontaneous ventricular event is detected during the first cardiac cycle, the capture parameter PxVs is measured with the short AVD (stage 38).

The following stage (stage 40) determines whether the configuration still did not change, i.e., atrial stimulation (A) did not become an atrial detection (P), or the reverse. In the event of change of configuration, the test is stopped and the algorithm returns to the initialization stage 30, because it is deemed not possible to carry out a conclusive test. If the configuration of the atrium did not change, then the AVD value is restored to its programmed value AVDp, and the algorithm seeks the occurrence of a possible spontaneous ventricular event during the following cardiac cycle (stage 42, and second cardiac cycle of FIG. 3).

If such a spontaneous event is detected (stage 44), it is not possible to measure the parameter of capture PxVp for the programmed AVD. The algorithm is thus completed with a "non conclusive" result. If no spontaneous ventricular event is detected during the second cardiac cycle, the capture parameter PxVp is measured with this programmed AVD (stage 46).

If the configuration did not change (stage 48), the AVD is lengthened and the algorithm with the value AVDl seeks the occurrence of a possible spontaneous ventricular event during the following cardiac cycle (stage 50, and third cycle of FIG. 3). If such a spontaneous event is detected (stage 52), this means that there was ventricular stimulation for AVDs and AVDp, but ventricular detection for AVDl.

The two values PxVs and PxVp that were measured at stages 38 and 46 are then compared. If these two values are close, the algorithm considers that the patient is stimulated for the value of the programmed AVD; conversely, it considers that the patient is in fusion if these two values are not close. Here and in what follows, it should be understood that "close" values are typically within a ±20% tolerance of each other (this tolerance value not being of course at all limiting in that other tolerance measures could be used).

Lastly, the absence of ventricular detection during the third cardiac cycle means that there was a ventricular stimulation for the three cycles with AVD short, AVD programmed and AVD long.

The parameter of PxVl capture is then measured (stage 54) and the three values, PxVs, PxVp and PxVl, are compared one to the next as between them (stage 56). If the three values are close (with the meaning indicated above) two by two, the algorithm shows an absence of a spontaneous rhythm and fusion; if PxVc and PxVp are close but PxVp and PxVl are not close, the algorithm shows an absence of fusion for the programmed AVD but a presence of fusion with the long AVD; if PxVp and PxVl are close but PxVs and PxVp are not close, the algorithm shows a fusion with the programmed AVD and with the AVD long, and a complete capture with the AVD short; if none of the three values PxVs, PxVp and PxVl are close, two by two, the signal is very variable according to the AVD and the algorithm considers that there is fusion for all the stimulations. The result is "non conclusive" and undoubtedly reveals an important intrinsic variability in the patient.

It should be understood that the present invention is preferably implemented in software of a microprocessor controlled implantable medical device, to acquire the indicated cardiac activity and process that activity to determine cardiac events. Suitable devices include, but are not limited to the aforementioned Talent™ pacing device. Advantageously, the present invention can be downloaded to an already implanted device by an external programmer, in a conventional manner, as software instructions to modify the operation of the already implanted device, for such devices that are able to receive software instructions and to modify its operation in response thereto.

One skilled in the art will appreciate that the present invention can be implemented by embodiments other that the particular embodiments disclosed, which are presented for purposes of illustration, and not of limitation.

We claim:

1. An active implantable medical device, in particular a pacemaker, defibrillator, cardiovertor or a multisite device, comprising:

means for detecting atrial events;

means for detecting ventricular events;

means for delivering an atrial stimulation;

means for delivering a ventricular stimulation, said means being able to deliver a ventricular stimulation pulse (V) after a programmed atrio-ventricular delay (AVD) following a detected atrial event and in the absence of detected ventricular event within said AVD; and means for detecting a fusion situation, said fusion situation detecting means being able to:

analyze a sequence of successive cardiac cycles by modifying the AVD from a first cardiac cycle to a following cardiac cycle, and detect the presence or the absence of a spontaneous ventricular event occurring inside the modified AVD; and means for determining an existence of a risk of fusion response to a detected spontaneous ventricular event during at least one of the cardiac cycles of the sequence.

2. The device of claim 1, wherein the AVD is modified by successive lengthening of its duration during the successive cardiac cycles, and the sequence includes at least three cardiac cycles.

3. The device of claim 1, wherein the AVD is modified by shortening and lengthening of the duration of the programmed atrio-ventricular delay, and the sequence includes at least three cardiac cycles having a short AVD, a programmed AVD and a long AVD respectively.

4. The device of claim 3, further comprising means for evaluating a capture parameter, and wherein the fusion situation detection means comprises means for acquiring a capture parameter for each cardiac cycle during the successive cycles of the sequence, and means for comparing the acquired capture parameters, two by two, wherein the fusion risk existence means determines the existence of a risk of fusion when at least two of the acquired capture parameter values are within a percentage of tolerance.

5. The device of claim 3, wherein the fusion situation detection means further comprises means for controlling, on each cardiac cycle, the stability of the atrial configuration, stimulated or spontaneous, and means for inhibiting the analysis of the sequence of successive cardiac cycles in response to a determined change of the configuration.

6. The device of claim 1, further comprising means for evaluating a capture threshold parameter, where in the fusion situation detection means operates to inhibit the automatic measurement of the capture threshold in the event of proven existence of a risk of fusion.

* * * * *